(12) United States Patent
Wolz (10) Patent No.: US 11,147,655 B2
(45) Date of Patent: Oct. 19, 2021

(54) METHOD FOR PRODUCING AN IMPLANT BLANK

(71) Applicant: WDT-Wolz-Dental-Technik GmbH, Bad Sobernheim (DE)

(72) Inventor: Stefan Wolz, Bad Sobernheim (DE)

(73) Assignee: WDT-Wolz-Dental-Technik GmbH, Bad Sobernheim (DE)

( * ) Notice: Subject to any disclaimer, the term of this patent is extended or adjusted under 35 U.S.C. 154(b) by 913 days.

(21) Appl. No.: 15/833,122

(22) Filed: Dec. 6, 2017

(65) Prior Publication Data

US 2018/0153662 A1 Jun. 7, 2018

(30) Foreign Application Priority Data

Dec. 7, 2016 (EP) ..................................... 16202698

(51) Int. Cl.
*A61C 13/00* (2006.01)
*C04B 41/87* (2006.01)
(Continued)

(52) U.S. Cl.
CPC ........ *A61C 13/0022* (2013.01); *A61C 8/0012* (2013.01); *A61C 8/0018* (2013.01);
(Continued)

(58) Field of Classification Search
CPC .... A61L 27/00–10; A61L 27/56; A61L 27/58; A61C 13/0022; A61C 13/0004;
(Continued)

(56) References Cited

U.S. PATENT DOCUMENTS 6,033,582 A * 3/2000 Lee ..................... A61L 27/3839
204/192.32
2008/0241793 A1* 10/2008 Collins ................ A61C 8/0012
433/174

(Continued)

FOREIGN PATENT DOCUMENTS

CN 1080627 A 1/1994

OTHER PUBLICATIONS

Xiangming Li, Pute Wu, Delan Zhu, Fabrication and Properties of Porous Si3N4—SiO2 Ceramics With Dense Surface and Gradient Pore Distribution, Ceramics International 40 (2014), Sep. 23, 2013, pp. 5079-5084, ScienceDirect, www.sciencedirect.com.

*Primary Examiner* — Yogesh P Patel
(74) *Attorney, Agent, or Firm* — Frank H. Foster; Kremblas & Foster (57) ABSTRACT

A method for producing an implant blank (100), in particular a dental implant blank from a starting body, said implant blank (100) comprising at least one first area, which is a surface area (102), and a second area, which is a core area (101), wherein the surface area (102) has at least one bioactive surface material (502) and extends from at least one first surface (103) in the direction of the core area (101), and the core area (101) has at least one carrier material that can be subjected to mechanical load. The starting body has a porosity for controlling a targeted distribution of the bioactive surface material (502) within the starting body and is loaded with a solution (500) of the bioactive surface material (502) in a first step, which is a loading step. In a second step, which is a distribution control step, the distribution of the bioactive surface material (502) within the starting body is controlled such that the solution (500) has a higher concentration within the surface area (102) than within the core area (101), the control being effected by regulating one or more environmental parameters in a closed
(Continued)

US 11,147,655 B2

Page 2 environment (200), in particular by regulating the humidity and/or the pressure and/or the temperature.

15 Claims, 5 Drawing Sheets (51) Int. Cl.
| | |
|---|---|
| *C04B 41/50* | (2006.01) |
| *C04B 41/00* | (2006.01) |
| *A61K 6/78* | (2020.01) |
| *A61K 6/802* | (2020.01) |
| *A61K 6/818* | (2020.01) |
| *A61K 6/822* | (2020.01) |
| *A61K 6/824* | (2020.01) |
| *A61C 13/08* | (2006.01) |
| *A61C 13/083* | (2006.01) |
| *B05D 1/28* | (2006.01) |
| *B05D 3/02* | (2006.01) |
| *B05D 5/06* | (2006.01) |
| *A61C 8/00* | (2006.01) |
| *A61C 13/20* | (2006.01) |
| *B05D 3/00* | (2006.01) |
| *B28B 11/24* | (2006.01) |
| *C03C 19/00* | (2006.01) |
| *C03C 23/00* | (2006.01) |
| *C04B 111/82* | (2006.01) |
| *C04B 111/00* | (2006.01) |
| *A61L 27/04* | (2006.01) |
| *A61L 27/56* | (2006.01) |

(52) U.S. Cl.
CPC ...... *A61C 13/0004* (2013.01); *A61C 13/0006* (2013.01); *A61C 13/082* (2013.01); *A61C 13/083* (2013.01); *A61C 13/20* (2013.01); *A61K 6/78* (2020.01); *A61K 6/802* (2020.01); *A61K 6/818* (2020.01); *A61K 6/822* (2020.01); *A61K 6/824* (2020.01); *B05D 1/28* (2013.01); *B05D 3/007* (2013.01); *B05D 3/0254* (2013.01); *B05D 5/06* (2013.01); *B28B 11/243* (2013.01); *C03C 19/00* (2013.01); *C03C 23/0095* (2013.01); *C04B 41/009* (2013.01); *C04B 41/5048* (2013.01); *C04B 41/87* (2013.01); *A61C 8/005* (2013.01); *A61C 13/001* (2013.01); *A61L 27/047* (2013.01); *A61L 27/56* (2013.01); *C04B 2111/00405* (2013.01); *C04B 2111/00836* (2013.01); *C04B 2111/82* (2013.01)

(58) Field of Classification Search
CPC . A61C 13/0006; A61C 13/082; A61C 13/083; A61C 13/20; A61C 8/00–0098; A61K 6/802; A61K 6/822; A61K 6/824; A61K 6/78; A61K 6/818; C04B 2111/00405; C04B 2111/00836; C04B 41/009; C04B 41/5048; C04B 41/87
See application file for complete search history.

(56) References Cited

U.S. PATENT DOCUMENTS

| | | | | |
|---|---|---|---|---|
| 2009/0061387 A1* | 3/2009 | Lomicka | ............... | A61C 8/0018 433/173 |
| 2009/0118114 A1* | 5/2009 | Zhang | .................... | A61L 27/10 501/135 |
| 2012/0095558 A1* | 4/2012 | Wooley | ................... | A61L 27/32 623/16.11 |
| 2012/0214128 A1* | 8/2012 | Collins | ................ | A61C 8/0006 433/173 |

* cited by examiner

METHOD FOR PRODUCING AN IMPLANT BLANK

BACKGROUND OF THE INVENTION

The invention relates to a method for producing an implant blank, in particular a dental implant blank from a starting body. An implant blank is understood to mean in particular the implant not yet densely or end-sintered. The implant blank comprises at least a first area, which is a surface area, and a second area, which is a core area, wherein the surface area extends from at least one first surface in the direction of the core area. Preferably, the surface area comprises the first surface of the implant blank as well as a near-surface volume arranged thereunder and, in particular, merges seamlessly with the core area, wherein the core area is arranged in the interior of the implant blank. The surface area has at least one bioactive surface material, and the core area has at least one carrier material that can be subjected to mechanical load.

In medical technology, a variety of implants are known, which are produced from implant blanks. These are intended to be implanted in the human body and there to take over the body's functions. The implants may be produced from various ceramic and/or metallic biocompatible materials. Biocompatible materials (e.g., alumina, zirconia, plastic implants, titanium, niobium, and tantalum, and their alloys) are exogenous materials that harmonize with the tissue of the recipient and do not trigger unacceptable reactions, such as rejection reactions. So-called permanent implants, which should remain in the body for at least a longer period of time or permanently, usually have a bioactive surface or outer surface which comprises a bioactive material. Bioactive materials (e.g. calcium phosphate ceramics such as hydroxyapatite, tricalcium phosphate, glass ceramics) trigger specific, biological reactions in the organism, resulting in a chemical bond between the implant and the surrounding tissue, in particular bones. These are endogenous materials, which interact with surrounding body structures and in this way are healing into the body of the patient. Furthermore, a distinction is made between bone-resorbing and non-bone-resorbing materials. Bone-resorbing materials contain calcium and/or magnesium, which is used by the body to regenerate bone structure. The core area of an implant comprises a material that can be subjected to mechanical load, preferably a biocompatible material (e.g. zirconia ceramics or titanium), which is suitable for absorbing forces and/or momenta which normally act on the body structure to be replaced at this point.

Dental implants are generally understood to mean implants used in the field of dentistry. In particular, dental implants may be tooth root implants, i.e., implants that replace the root of a tooth and which are implanted in the maxillary crest of the patient. Another example is bone replacement materials, such as maxillary crest implants, which replace portions of or even the entire maxillary crest of the patient. Tooth root implants, i.e., artificial tooth roots consist of an implant body, which is regularly formed as a screw with external thread and is provided for insertion or for screwing into the jawbone or the maxillary crest. A transition section of the implant, which is arranged in the area of the gums of the patient, is followed by a so-called structural unit, also called abutment. The abutment serves as an attachment for the actual dental prosthesis, for example, a dental crown, a bridge or the like. The abutment may be implemented integrally with the implant body and the transition section, i.e., in one piece, or in two pieces, i.e., screwed into the transition section. The dental implant is preferably produced from a biocompatible, metallic and/or ceramic material. In dental technology, titania or zirconia is usually used, but also other tissue-compatible, biocompatible ceramics, (dental) metals and metal alloys. Further information on (dental) implants can be found in the following standards: ISO 14801:2016 "Dentistry—Implants—Dynamic loading test for endosseous dental implants"; DIN EN ISO 5832-3:2015-06—Draft "Chirurgische Implantate—Metallische Werkstoffe [engl. Surgical implants—Metallic materials]"; DIN EN ISO 5832-2:2012-08 "Chirurgische Implantate—Metallische Werkstoffe [engl. Surgical implants—Metallic materials]", DIN EN ISO 16498:2013-12 "Zahnheilkunde—Mindestdatensatz bei der klinischen Anwendung von Dentalimplantaten [engl. Dentistry—Minimum dataset for the clinical use of dental implants]"; DIN EN 1642:2012-06 "Zahnheilkunde—Medizinprodukte für die Zahnheilkunde—Dentalimplantate [engl. Dentistry—Medical devices for dentistry—Dental implants]"; DIN EN ISO 13356:2016 "Chirurgische Implantate—Keramische Werkstoffe aus yttriumstabilisiertem tetragonalem Zirkoniumoxid (Y-TZP) [engl. Surgical implants—Yttria-stabilized tetragonal zirconia (Y-TZP) ceramic materials]"; ISO 13779-3: 2008 "Implants for surgery—Hydroxyapatite".

In order to achieve an improved retention of the dental implant within the bone and/or tissue structure of the patient, the implant body of a dental implant blank, i.e., the part to heal into the maxillary crest of the patient, is subjected to a surface optimization to increase biocompatibility. For this purpose, a distinction is generally made between a chemical/mechanical treatment of the surface and a coating of the surface of the implant blank.

From DE 10 2007 007 865 A1 a method for producing implants with an ultrahydrophilic surface is known. Surfaces with a high surface energy may have a strong tissue bioadhesion that promotes healing of the implant into the organism. Surfaces with a high surface energy usually have low contact angles with water, which in turn are characteristic of a high wettability of the surface. To produce such an ultrahydrophilic surface, the surface of a metal implant is treated with an oxidizing agent to form an oxide layer. The treatment is continued until a contact angle hysteresis of less than 5° is obtained.

EP 2 046 235 B9 describes an etching method for generating a surface structure on the outer surface of a post element, i.e., of the implant body of a dental implant. For this purpose, the post element of the implant blank, which is produced from an yttrium-stabilized zirconium ceramic, is subjected to an etching process, whereby selectively individual components are extracted from the surface of the post element. Where the components have been extracted pores in the nanometer range form, which facilitate the ingrowth of surrounding bone/tissue.

For example, from WO 2014 110 997 A1 it is known to roughen the surface of an implant blank by means of sandblasting or grinding and to etch in order to improve the osseointegrative properties of the implant surface. In this case the surface of the blank is provided with a surface structure, which facilitates the healing of the surrounding bone into the implant. However, during final end- or densely sintering by which the blank obtains the desired mechanical strength and becomes the finished dental implant, tensions and microcracks often occur due to abrasive surface processing, rendering the dental implant unusable and/or result in high complaint rate. To solve this problem, WO 2014 110 997 A1 proposes to provide the roughened surface of the implant blank elaborately with a coating. For this purpose, a material is first applied to the roughened, biocompatible surface of the implant blank. The blank is then subjected to a heat treatment, wherein the material penetrates into the bioactive surface of the blank to improve the mechanical strength. A change in the previously generated surface roughness and a concomitant deterioration of the physical properties should principally be avoided.

DE 101 19 096 A1 discloses a biologically functionalized coating of an implant surface. The coating is applied in a layer thickness on an open-pored substrate surface, which does not affect the open porosity and thus the structural properties of the substrate surface. Open-pore substrate surfaces can be produced for example by known sintering, casting and spraying techniques. For metallic substrates, one or more plasma-sprayed, corrosion-chemically optimized titanium layers can be applied to the base body. The substrate surface should have a pore size between 75 and 500 μm, the porosity should be between 15 and 40%, to allow an optimal healing into bone structure.

From WO 2015 168 332 A2 a method for generating surface structures on an implant surface is known. The structuring improves the osseointegrative properties of the surface, thereby enabling improved bone ingrowth. The surface structuring is already generated during the production of the implant blank. The blank can be produced, for example, by powder compacting, slip casting, injection molding or spark plasma sintering. Before the blank is densely or end-sintered, its structured surface can be immersed in an aqueous solution containing ions and/or particles. At least a portion of the ions and/or particles enter the structured surface and become trapped by the final sintering process.

A disadvantage of the methods described above is that the treatment results in a weakening of the mechanical properties of the implant surface or of the implant body. In particular, this can lead to microcracks, which lead to damage during further processing of the implant blank or even during later use of the implant.

Another option for generating a biocompatible surface of an implant are the so-called coating methods. For this purpose, the surface of the implant body is provided, for example, with biocompatible and/or bioactive composite materials for generating a highly porous, optionally bioactive surface coating. Usually, a bioinert, but mechanically stable volume material is used as the main mass of the implant and coated with a surface material. A disadvantage of the coating method is that a bond that can be subjected to mechanical load must be achieved between the implant surface and the coating in order to prevent the coating from flaking off. In case of flaking off, the implant will detach from the surrounding tissue and must be surgically removed.

For coating the implant surface, in particular, bioactive calcium phosphates such as hydroxyapatite (HAp) can be used, which are similar to the mineral constituent of biological hard tissue, such as bone, dentin and enamel. The coating with HAp takes place, for example, by thermal plasma spraying. In this case, powdered HAp is heated by means of a plasma flame above 1650° C. and applied to the implant surface with high pressure. The HAp particles cool on the implant surface and solidify as a solid, crystalline layer. Alternative options for coating implant surfaces include sputtering, biomimetic coating methods, electrochemical, electrolytic and electrophoretic coatings as well as sol-gel, rotary and dip-drawing methods (Friederike Kraas, "Ober die Herstellung einer Oberflachenbeschichtung aus Hydroxylapatit mittels Sol-Gel-Synthese and Untersuchungen hinsichtlich ihrer in-vitro-Biokompatibilität [engl. On the preparation of a surface coating of hydroxyapatite by sol-gel synthesis and studies regarding its in vitro biocompatibility]", Dissertation, Kiel, 2014).

From DE 10 2013 102 370 A1, for example, a method for producing a functionalized implant is known. The implant surface is coated with a biocompatible material which is suitable for generating a highly porous surface. The coating is carried out, for example, by PVD, CVD methods or by electrochemical processes. Due to the porous coating, healing of the surrounding bone and/or tissue structure into the implant is favored. In order to achieve better adhesion between the highly porous coating and the implant surface, the implant surface can be roughened by abrasive surface treatment before application of the coating. The method described is also suitable for producing dental implants.

A disadvantage of the coating methods described is that a sufficiently stable bond can not be generated between the coating and the implant surface, which can lead to flaking off of the coating and thus to the loss of the implant.

It is therefore an object of the present invention to provide an improved production method for an implant blank, in particular a dental implant blank, having a bioactive surface. It is a further object of the invention to provide an improved implant blank, in particular a dental implant blank with a bioactive surface.

The object is achieved by a method according to claim 1 and by an implant blank which has been produced in particular by the method according to the invention.

Advantageous, optional embodiments and/or developments arise wholly or partly from the dependent claims.

SUMMARY OF THE INVENTION

A method according to the invention of the type described above is characterized in that the starting body has a porosity for controlling a targeted distribution of the bioactive surface material within the starting body. As a starting body, in particular in the dental industry, a porous, conventional ceramic and/or metallic blank/white compact/green compact/brown compact can be used, which has been produced, for example, by pressing from ceramic powder or metal powder, by slip casting from ceramic or metallic slip, by means of a ceramic 3D printer, by laser sintering (SLM), injection molding or another suitable method. When a ceramic starting body is used, it can be stabilized in particular with yttrium and/or calcium and/or cerium, the proportion of the stabilizing component in the surface area being lower than in the core area, as a result of which the core area has increased mechanical stability.

In order to control a targeted distribution of the bioactive surface material within the starting body, the starting body must have a porosity, i.e., the starting body is not densely or end-sintered. The porosity of the starting body is in a range between 3% and 90%, preferably in a range between 25% and 30%. The porosity results from the ratio of the bulk density of the starting body to its true density multiplied by 100%.

In a first step, which is a loading step, the starting body is loaded with one or more solutions of the bioactive surface material. Loading is understood to mean the infiltration of the solution, i.e., the solvent (dissolver) with the bioactive surface material (solvate) dissolved therein, into the interior, in particular also into the core area of the starting body.

In a second step, which is a distribution control step, the distribution of the bioactive surface material within the starting body is controlled such that the solution has a higher concentration within the surface area than within the core area. The distribution can also be controlled so that the concentration in the core area is zero. In particular, a higher concentration of the solution means that there is more solution in the pores of the starting body, but also a higher concentration of the solvate within the dissolver. Preferably, a uniform concentration profile is generated between the surface and the core area. The profile may be formed two-dimensionally or three-dimensionally.

After the starting body has been loaded with the solution of the bioactive surface material, the bioactive surface material can be distributed as desired within the entire volume of the starting body. The control of the distribution of the bioactive surface material is effected by regulating one or more environmental parameters in a closed environment, in particular by regulating the humidity and/or the pressure and/or the temperature. A closed environment is understood to mean an environment that forms a closed system, e.g. a vessel, cabinet, room or similar, which is sealed against the outer environment. This allows a targeted regulation of the environmental parameters. A regulation is understood to mean not only a quantitative regulation, but also a regulation with regard to defined, local areas within the environment, i.e. one or more environmental parameters can be applied to the starting body with respect to different surfaces and/or surface areas. The one or more loading steps and the one or more distribution control steps may be sequential or (partly) simultaneous.

Preferably, the loading of the starting body with the solution of the at least one bioactive surface material is effected via a second surface of the starting body, which is a loading surface, and which is different from the first surface. I.e., the solution of the bioactive surface material is infiltrated during the loading step via a second surface, a loading surface, into the interior, in particular the core area of the starting body. During the distribution control step, the solution is supplied to the surface area extending from the first surface in the direction of the core area and/or to the first surface itself.

According to a preferred variant of the method, the loading surface is arranged outside the closed environment for loading the starting body with the bioactive surface material. In particular, the first surface of the starting body is located within the closed environment, whereas the second surface, the loading surface, is arranged outside the closed environment. The closed environment is sealed against the outer environment, for example, by means of a suitable seal, in particular a silicone gasket along the starting body.

According to an optional variant of the method, the concentration of the solution is kept constant during the loading step and/or during the loading of the starting body. I.e. the ratio of the amount, in particular the mass of the bioactive surface material to the total amount of solution, in particular the solution mass is kept constant. Preferably, the loading is effected by means of a loading reservoir and a loading body, wherein the loading reservoir has been previously filled with a fixed volume of the solution. The loading body is arranged within the loading reservoir and may comprise one or more loading zones. Each loading zone can either have a different solution and/or the same solution with different concentrations. The different solutions are preferably a solution with bioactive surface material, a solution with chemical substances for affecting physical properties, a solution with coloring components or even pure solvent. The loading zones can be arranged side by side for a parallel loading of the loading surface and be separated from each other, for example, by films. In the parallel loading different solutions and/or the same solution with different concentration is infiltrated into the starting body at the same time, but locally different. For a serial loading, the loading zones are arranged one below the other and not separated. In the serial loading different solutions and/or the same solution with different concentration is infiltrated into the starting body sequentially in time, but locally the same. The loading body comprises a capillary pressure-retaining material, in particular microfibers. The maximum loading time of the starting body is dependent on the solution volume and the size of the loading reservoir, respectively. In order to keep the concentration of the solvate constant within the solvent, i.e. the proportion of the bioactive surface material within the solvent, the loading reservoir is sealed from the outer environment as well as from the closed environment. In this way, evaporation of the solvent and thus an increase in concentration of the solution is prevented. In an alternative embodiment, the loading reservoir may have an inflow or an inflow and an outflow, in order to allow a continuous refilling of the solution but also a change of the solution concentration.

The distribution of the bioactive surface material within the starting body is effected in particular by a convection flow. In this case, a direction of flow and/or velocity of the solution is controlled by targeted generation of environmental parameter gradients within the closed environment. In particular, humidity differences and/or pressure differences and/or temperature differences with respect to different surfaces and/or with respect to different surface areas of the starting body are set.

According to an advantageous embodiment of the method, the speed of movement and/or the flow velocity of the solution is controlled by increasing and/or decreasing one or more of the environmental parameter gradients. For example, a first ambient pressure applied to one surface of the starting body may be increased and a second ambient pressure applied to another, opposing surface of the porous ceramic may be decreased or kept constant, thereby increasing the absolute value of the pressure gradient with respect to the two surfaces. This in turn leads to a change, in particular an increase in the speed of movement and/or the flow velocity.

According to a likewise advantageous embodiment of the method, a direction of movement and/or the direction of flow of the solution is controlled by changing the direction of one or more of the environmental parameter gradients. For example, the first ambient pressure can be applied to a surface of the starting body and the second ambient pressure to another surface of the starting body, whereby the direction of movement and/or a direction of flow between the surfaces of the starting body is controlled. By reversing the environmental parameter gradient profile (i.e., changing the sign of the gradient), the direction of movement and/or the direction of flow can be reversed.

In an optional variant of the method, at least a part of the first surface of the starting body is isolated and/or sealed from the closed environment during the distribution control step. In this way, the environmental parameters with respect to specified surfaces and/or surface subareas can be regulated locally. This serves for the targeted control of the distribution, in particular the targeted control of the direction of movement and/or the direction of flow. Additionally or alternatively, at least a portion of the second surface of the starting body is isolated and/or sealed from the outer environment and/or from the loading reservoir during the loading step. The isolation and/or sealing can be used during the loading step for locally targeted loading of the starting body.

Advantageously, a seal and/or isolation is effected by means of a mold, a housing or the like and/or a film and/or a coating. For example, the mold may be a silicone mold, the film may be a self-adhesive film, and the coating may be a silicone, latex, and/or wax coating.

In an advantageous variant of the method, the control of the concentration and/or of the concentration profile of the solution is effected within the starting body by drying and/or vaporization. Concentration of the solution within the starting body is understood to mean the concentration of the solution, i.e. the amount of dissolved bioactive surface material relative to the total solution amount, but also the amount of solution that is located within the starting body, more precisely in the pores of the starting body. In particular, heat and/or air or an air flow is applied to the first surface or to at least a part of the first surface in order to achieve vaporization and/or evaporation and/or drying of the solution, in particular of the solvent. In this way, on the one hand the amount of solvate is increased, i.e., of the bioactive surface material relative to the dissolver, i.e., relative to the solvent. On the other hand, the solution flows from the core area of the starting body in the direction of the first surface or in the direction of the parts of the first surface, onto which heat and/or air is applied for control. In order to permit vaporization of the solvent on the first surface of the starting body, a connection, for example in the form of a valve for removing the vaporization, evaporation, and/or drying moisture, may be provided between the closed environment and the outer environment.

Preferably, the solution of the bioactive surface material is infiltrated into the starting body by means of the loading step and/or by means of the distribution control step in such a way that, starting from the first surface, a depth of infiltration of the bioactive surface material of at least 50 µm is achieved. In particular, the entire volume of the starting body is loaded with the solution. By means of the distribution control step a flow from the core area in the direction of the surface area is generated, thereby controlling a targeted depth of infiltration from the first surface of the bioactive surface material. Alternatively, the loading of the starting body can be effected over individual subareas of the loading area, so that, for example, only the surface area is loaded with the solution of the bioactive surface material. In contrast to the methods known from the prior art, the distribution of the bioactive surface material within the porous starting body is not effected by diffusion from its surface towards the interior, rather conversely from its interior in the direction of the first surface. By this method, the depth of infiltration can be set in a targeted manner or a targeted profile of the concentration can be generated.

In a third, optional method step, which is a crystallization step, the bioactive surface material is crystallized. The bioactive surface material is a crystallizable material. For example, it may be hydroxyapatite (HAp), but also other biocompatible materials suitable for forming a bioactive surface. The crystallization is initiated in particular within the surface area and/or in the area of or starting from the first surface. To initiate the crystallization, a saturation, preferably a supersaturation concentration of the bioactive surface material within the solvent is generated in the desired area. In particular, by regulating the environmental parameters within the closed environment, the solution is controlled in such a way that a liquid film of solution forms on the first surface of the source body. The crystallization is initiated by vaporization and/or evaporation and/or drying of the solvent, whereby a solid crystal layer forms on the first surface of the starting body. Depending on the concentration set or concentration profile set, the bioactive surface material crystallizes within the pores of the surface area or up to the desired depth of infiltration within the pores of the starting body. By crystallization nuclei, so-called seed crystals within the pores in the surface area, the crystal formation can be accelerated and controlled in a targeted manner.

Due to the crystallization of the bioactive surface material within the pores of the starting body, in particular within the pores of the surface area, a form-fitting and/or force-fitting and/or frictional fitting of the bioactive surface material with the starting body is achieved. Depending on the pre-set depth of infiltration, a mechanically strong bond is generated between the crystalline layer and the starting body, such that flaking off of the layer, i.e., of the bioactive surface coating or damage to the implant blank can be avoided.

In an optional crystal growth step, crystals of the bioactive surface material grow, starting from the porosity, i.e., from the pores of the surface area and/or from the first surface, to form a crystalline layer. The crystalline layer completely covers the first surface of the starting body or covers at least parts of the first surface of the starting body. The crystal growth step is preferably effected as a fourth step following the crystallization step, wherein the layer thickness of the crystalline layer is increased. The preferred layer thickness of the crystalline layer is, after the end-sintering or densely sintering, on average between 0.10-250 µm in order to facilitate or accelerate healing of the implant into the surrounding tissue. However, it is easily possible to generate a layer thickness of up to 2000 µm. The layer thickness is dependent on the crystallization time, i.e., the duration of the crystal growth step, the concentration of the bioactive surface material in the solution and the type of solvent used. In contrast to the methods known from the prior art, the crystalline, bioactive surface coating is not applied from the outside to the implant body, rather formed from its interior by crystal growth, since the bioactive surface material is already in the pores of the starting body.

According to a preferred embodiment of the method, the crystal growth step is effected continuously, wherein the loading step is carried out at least partially simultaneously. Continuously is understood to mean in particular that the loading and the crystal growth are effected at least at times at the same time, wherein solvent with the bioactive surface material, by means of the loading reservoir, is continuously supplied to the loading surface and taken up by it. In the continuous method, the solvent including the bioactive surface material and/or the chemical substances for affecting the physical properties or coloring, or also pure solvent, is first supplied to the loading body which is arranged in the loading reservoir, or to the corresponding loading zones of the loading body. Subsequently, said solvent is taken up by the loading surface by parallel or serial loading. By regulating the environmental parameter gradients within the closed environment, the solvent with the respective solvate is directed to the desired area, particularly the surface area. Starting from the pores of the surface area or from the surface of the implant blank, the solvent is evaporated and/or vaporized and/or dried, wherein the bioactive surface material forms a solid, crystalline layer starting from the surface. The evaporated and/or vaporized and/or dried solvent is discharged from the closed environment into the outer environment and continuously replaced by loading via the loading surface from the loading reservoir. The liquid volume of the evaporated and/or vaporized solvent corresponds to the volume of the solvent including the bioactive surface material dissolved therein, the volume of which is taken up by the loading surface.

In an optional pore-forming step, the crystals and/or the crystalline layer of the bioactive surface material are subjected to a heat treatment to form pores and/or to increase the surface roughness. The bioactive surface coating formed by means of the bioactive surface material already has a sufficient roughness, which ensures a healing of the surrounding tissue, in particular of the jaw bone, into the pores. In order to increase the roughness and/or the number of pores or the pore size, after forming the bioactive surface coating, the implant blank may be subjected to a heat treatment at a temperature in a range of 500-800° C. Preferably, the diameter of the pores of the crystalline surface coating is in a range between 50 and 200 μm.

Advantageously, a morphology and/or structure and/or surface and/or porosity, in particular number and size of the pores, the crystalline layer and/or the crystals of the bioactive surface material may be affected by means of the solvent, i.e. by the choice of solvent during the method.

A suitable solvent is, for example, water, in particular distilled water. By using ethanol, flatter and denser crystalline layers can be generated. Ethanol has a higher evaporation or vaporization rate than water, whereby the crystal formation proceeds faster. A higher surface roughness can be achieved, for example, by the use of acetic acid as a solvent. However, it is also conceivable to use other solvents for affecting crystal formation.

In an optional coefficient of thermal expansion balancing step, the starting body is rinsed with a balancing solution having zirconium and/or calcium and/or cerium. The coefficient of thermal expansion (CTE) indicates the factor by which a body expands per temperature change (in Kelvin). By rinsing the starting body with a solution containing in particular zirconium and/or calcium nitrates, a CTE profile can be set between the surface area and the core area of the starting body or of the implant blank. A rinse is understood to mean a loading of the solution and a subsequent control of the distribution of the solution within the starting body. Preferably, a coefficient of thermal expansion profile is set from the core area to the surface, preferably from CTE=14/K to 9/K. For a targeted distribution of the balancing solution, it can be made use of the fact that part of the pore volume of the starting body is already filled with the biocompatible surface material. The starting body has a decreasing concentration profile of the biocompatible surface material from its surface towards its core area, whereby a subsequent rinsing of the starting body with the balancing solution leads to a reverse concentration profile of the balancing solution. The coefficient of thermal expansion balancing step further reduces the likelihood of the bioactive crystalline surface layer flaking off the surface of the starting body during a subsequent heat treatment and/or a densely or end-sintering step. A steady profile of the coefficient of thermal expansion balances the thermal volume expansion difference between the core area, the surface area and the bioactive, crystalline surface coating.

According to an advantageous variant of the method, an absorption capacity of the starting body or an absorption capacity of individual areas of the starting body is controlled by a loading of pure solvent. In particular, for example, the core area of the starting body before and/or during loading with the solution containing the biocompatible surface material can be loaded specifically with pure solvent, for example ethanol and/or acetic acid and/or distilled water in order to avoid or reduce penetration of the biocompatible surface material into the pores of the core area. Alternatively, the absorption capacity of the pores of individual areas of the starting body can be selectively controlled by gas inclusions, in particular air inclusions.

According to an optional variant of the method, at least one carrier material of the porous starting body is crystallizable, wherein the crystal formation of the crystallizable carrier material is not completely completed. The crystallizable carrier material may be, in particular, zirconium or other ceramics or metals or metal alloys suitable for dental technology.

In an optional freeze-drying step, the bioactive surface material is fixed in the pores of the desired areas of the starting body. In this way, in particular a back diffusion of the bioactive surface material into the interior of the starting body can be hindered. The freeze-drying step preferably takes place under vacuum.

In an optional sintering step, a material bond and/or a chemical bond is generated between the bioactive surface material and the carrier material that can be subjected to mechanical load. By means of a sintering process, in particular in the range of temperatures around 1450° C., the bioactive surface material, which is arranged in the pores of the starting body, melts with the carrier material that can be subjected to mechanical load, whereby the material bond and/or chemical bond is achieved. In particular, both the bioactive surface material or the carrier material that can be subjected to mechanical load are crystallizable or have at least crystallizable components whereby a common crystal structure is formed and the composite stability is increased. The optional sintering step can also be a end- or densely sintering of the implant blank, which makes it the finished implant.

In an alternative embodiment of the method, the porous starting body comprises an inert metal or preferably consists of an inert metal, in particular a dental metal. Inert metals such as, for example, titanium are particularly well suited for the production of implants, since these form an oxide layer on their surface, whereby surrounding bones and tissues are not rejected. Dental metal is understood to mean metals which are suitable for producing dental prostheses or implants in the dental area.

The method according to the invention is preferably used for producing implant blanks from starting bodies which already have the desired implant shape. However, it is likewise possible to control the distribution of the biocompatible surface material within a, for example, plate-shaped blank, to mill the blank into the desired spatial shape by means of a CAD/CAM milling machine, and then to subject it to the crystal formation and/or crystal growth step. In this way, multiple implant blanks can be produced from one starting body.

During loading with and/or the control of the bioactive surface material within the starting body, a loading and/or control with different chemical substances for affecting the physical properties of the implant blank and/or for coloring or for generating a two-dimensional or three-dimensional color profile can take place simultaneously.

The object of the invention is further solved by an implant blank, in particular produced by the method according to the invention. The implant blank is suitable for producing a bioactive implant, in particular a dental implant, and has at least one first area, which is a surface area, and one second area, which is a core area. The surface area comprises a bioactive surface material and the core area comprises a carrier material that can be subjected to mechanical load. Starting from a first surface, the implant blank comprises a crystalline layer having the bioactive material. The crystalline layer is form-fittingly and/or force-fittingly connected to the surface area, wherein the bioactive surface material is arranged within pores of the surface area. Between the bioactive surface material and the carrier material that can be subjected to mechanical load a material bond and/or a chemical bond may additionally be present.

A depth of infiltration of the crystalline layer in the pores of the surface area is at least 50 µm, preferably at least 75 µm and particularly preferably at least 100 µm. The higher the depth of infiltration of the biocompatible surface material, the stronger is the mechanical and/or firmly bonded and/or chemical connection to the carrier material, whereby a flaking off of the crystalline layer is prevented. Preferably, the amount of bioactive surface material arranged within the pores steadily and/or uniformly decreases from the surface of the body toward its core area.

Further details, features, feature (sub)combinations and effects based on the invention will become apparent from the following description of preferred exemplary embodiments of the invention and from the drawings.

DETAILED DESCRIPTION OF THE INVENTION

Figure 1:
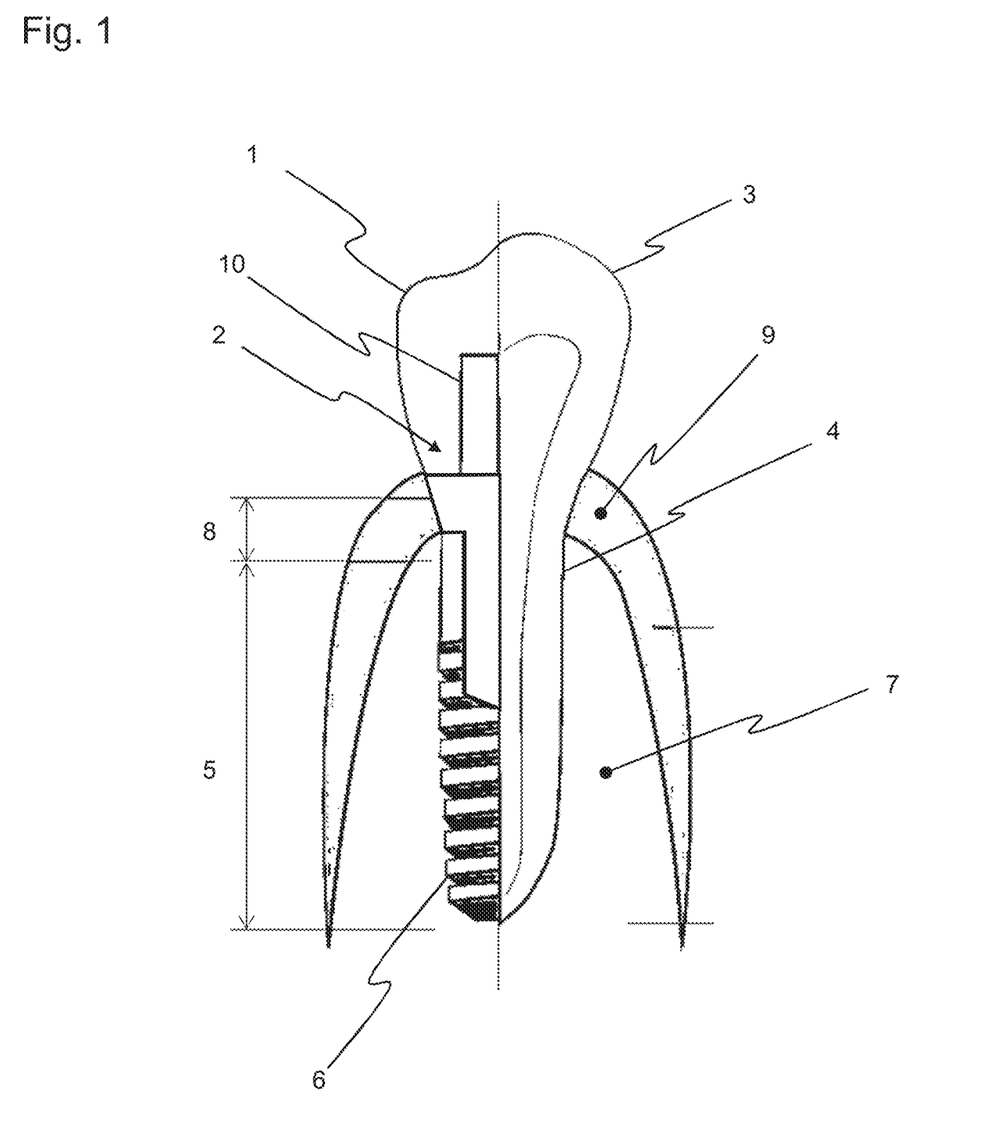
FIG. 1 shows a schematic representation of a dental implant which is screwed into the jawbone of a patient for receiving a dental prosthesis.

FIG. 1 schematically shows a dental prosthesis 1, in particular a crown, with a dental implant 2 arranged thereunder, compared to a tooth 3 with underlying tooth root 4. The dental implant 2 comprises an implant body 5, which is provided with an external thread 6 and is provided for screwing into the jawbone 7 of a patient. Above the implant body 5 there is a transition section 8 which, depending on the design of the dental implant 2, can be made in one piece therewith or, as shown here, is screwed into the implant body 5. The transition section 8 is arranged within the gums 9 of the patient. The transition section 8 adjoins the so-called abutment 10, which protrudes from the gums 9 of the patient and is configured to receive the dental prosthesis 1. The surface of the implant body 5 is preferably configured as a bioactive surface, so that the surrounding jaw bone 7 can heal into the implant body 5. The transition section 8, which is arranged within the gums 9, should have as smooth as possible, non-porous surface of a biocompatible material to prevent ingrowth of the gums and the colonization and multiplication of bacteria.

Figure 2:
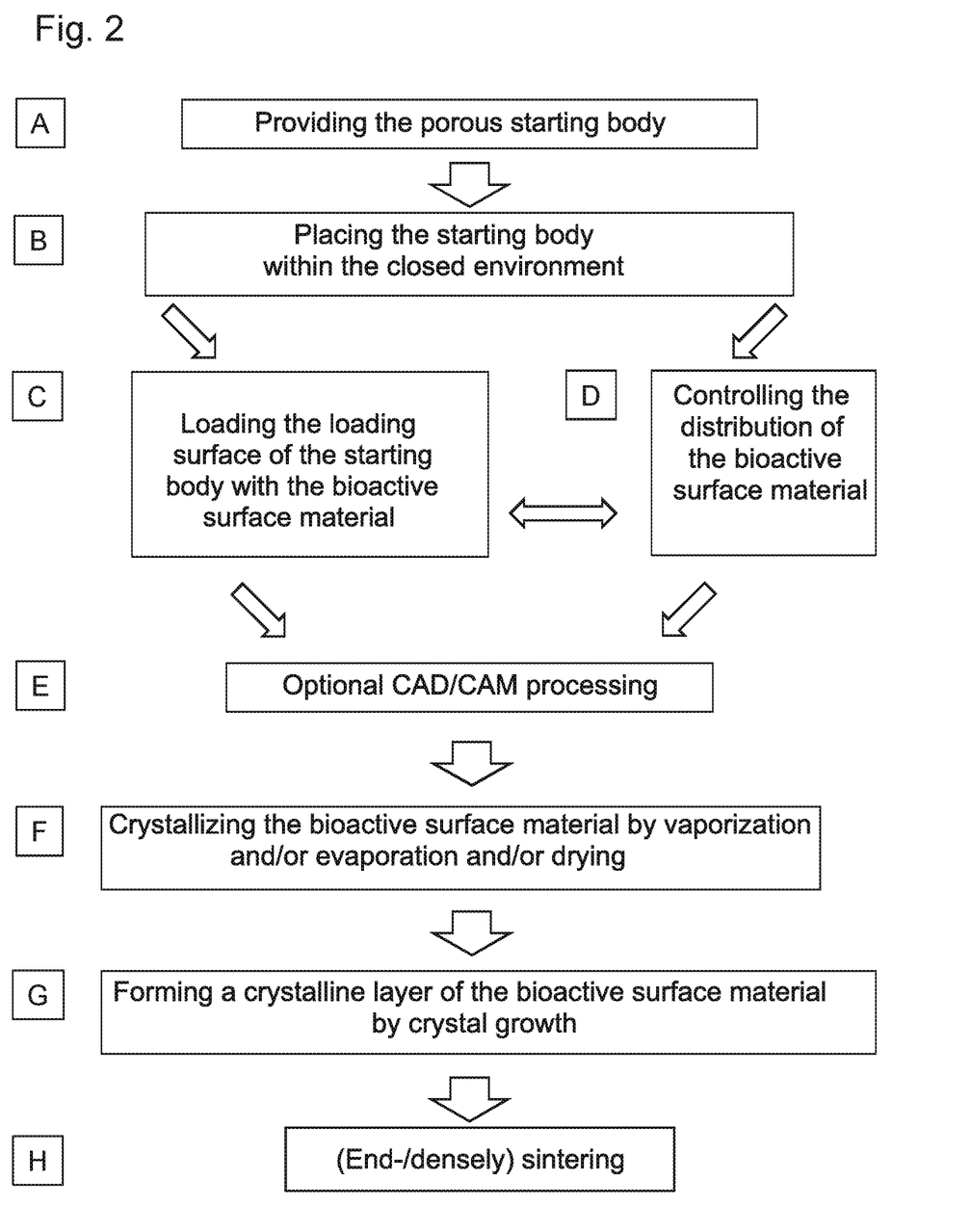
FIG. 2 shows a flow chart for a schematic representation of the sequence of an exemplary production method according to the invention.

FIG. 2 shows a method sequence according to the invention by way of example with reference to a flow chart. In a first step (A), a porous starting body, for example, a cylindrical zirconia ceramic blank having a diameter of 16.5 mm, a height of 16 mm and a total mass of 10.32 g is provided. The starting body is placed in a closed environment in a second step (B). This can be a cylindrical chamber. A first surface of the starting body, at which the formation of a bioactive surface coating is to take place, is arranged completely within the closed environment, wherein a second surface or at least a part of the second surface, which is a loading surface, is arranged outside the closed environment. In a third step (C), the loading surface of the starting body is loaded with a solution of a bioactive surface material. The solution is a hydroxyapatite sol prepared by dissolving 2.5 g of calcium nitrate and 1.5 g of triethyl phosphate in 40 g of ethanol. The precursors of the sol are present in the ratio $Ca/PO_4 = 1\%$. The maximum absorption capacity of the pores of the zirconia ceramic blank is 1.55 g of the solvate. Simultaneously with or subsequent to the loading (C), the distribution (D) of the bioactive surface material is effected, the solution having a higher concentration within the surface area than within the core area. For controlling, at least one environmental parameter, in particular the humidity and/or the pressure and/or the temperature is regulated for generating environmental parameter gradients. Preferably, a temperature of 25° C. and a humidity of 30% are set in the chamber, resulting in a temperature or humidity gradient between the first surface and the loading surface. In an optional CAD/CAM processing step (E), the cylindrical ceramic blank can be milled into the desired spatial form. The distribution of the bioactive surface material may be controlled prior so as to give volume areas with increased concentration of the bioactive surface material within the starting body. These areas preferably become outer surfaces or surfaces of an implant blank by the subsequent milling. In a crystallization step, the bioactive surface material is crystallized, whereby the concentration of the solution within the surface area is increased by vaporization and/or evaporation and/or drying up to a saturation concentration. During a crystal growth step (F), a crystalline layer of the bioactive surface material is formed starting from the first surface of the starting body. Depending on the desired layer thickness and structure of the crystalline surface coating, the growth phase takes for example, three days within the closed chamber. To terminate the crystal growth, the starting material is rinsed for a further two days with pure solvent, preferably ethanol, in order to remove residues of the hydroxyl apatite sol, in particular from the core area of the starting body. If the starting body was previously loaded by means of parallel loading, i.e., with a loading body having multiple loading zones arranged side by side, the need for rinsing can be avoided. By means of the parallel loading, it is possible to load the core area with a solution which in turn does not contain any bioactive surface material, while simultaneously supplying bioactive surface material to the surface area. In this way, the core area remains completely free of HAp residues during the method and also after completion of the dental implant, since the pores of the core area are "blocked" by taking up the HAp-free solution. Subsequently, drying for three days at 25° C. and 20% humidity can take place. By increasing the hydroxyapatite sol concentration, the crystal growth is accelerated, by increasing the duration of the crystal growth step, a higher layer thickness can be set. Another option in this context is to increase the drying time to 30 days at 22° C. and 40% humidity. A final end- or densely sintering turns the bioactively coated implant blank finally into the implant. The sintering takes place in a sintering furnace in a range of 1300-1600, usually at about 1450° C. (depending on manufacturer or material) for 4 hours. The sintering process causes calcification, resulting in a synthetic hydroxyapatite. A final heat treatment at 150-200° C. for an additional 4 hours is advantageous. For another 10-50 hours, a hydrothermal heat treatment should be included 150-200° C. to convert tricalcium phosphate (TCP) to hydroxyapatite (HAp).

Figure 3:
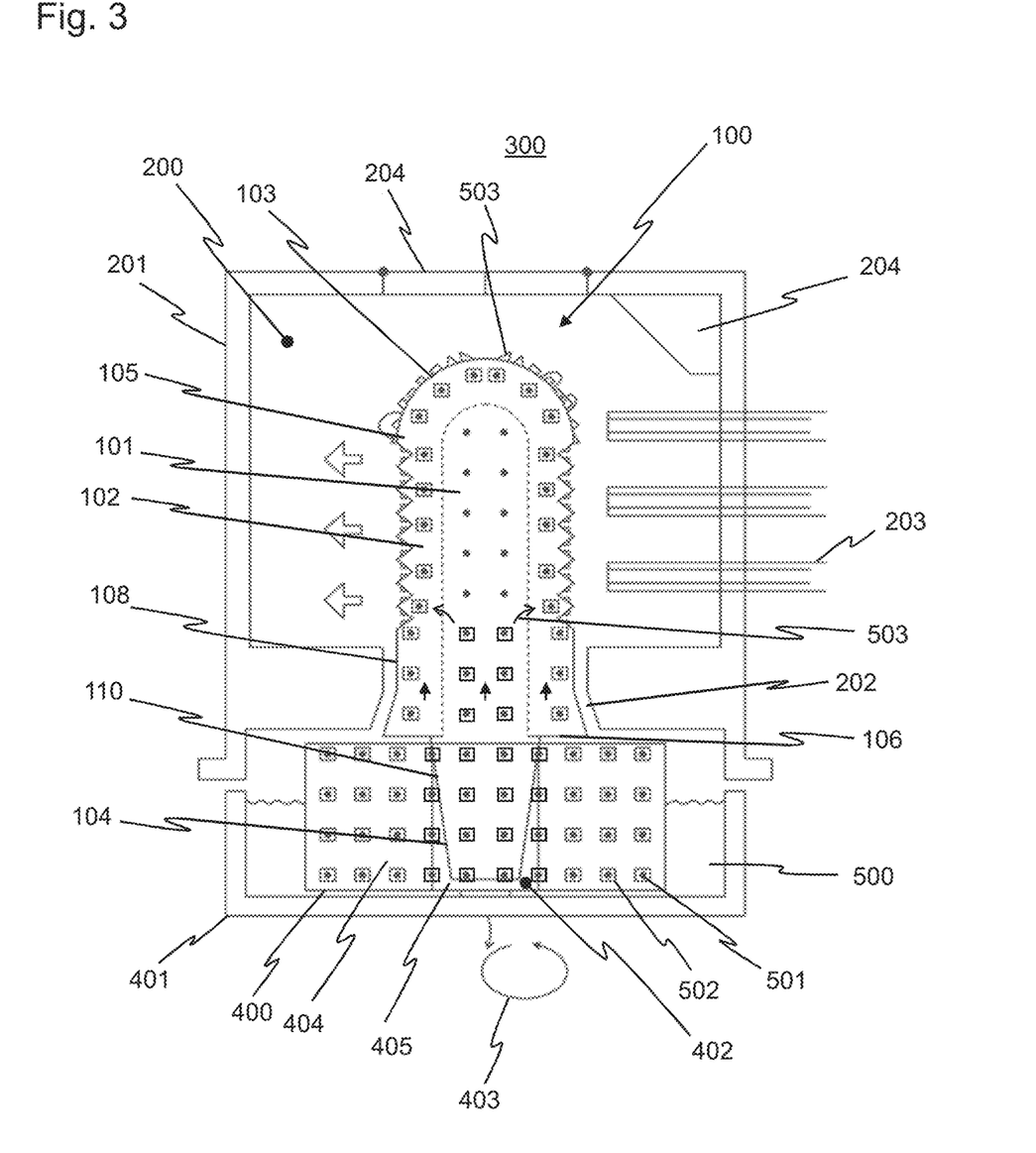
FIG. 3 shows a schematic representation of a dental implant blank which is arranged in a closed environment for the production method according to the invention, FIG. 4 schematically shows the growth of a crystalline bioactive surface coating.

FIG. 3 shows a schematic representation of a rotationally symmetrical dental implant blank or starting body 100, which is arranged in a closed environment 200. In the present example, the sealed environment 200 is configured as a chamber 201, but it could also be, for example, a cabinet or space for receiving multiple or a plurality of dental implant blanks 100. The dental implant blank 100 is configured in one piece and has an implant body 105, a transition section 108 and an abutment 110. Furthermore, the dental implant blank 100 comprises a core area 101 and a surface area 102 which, starting from a first surface 103, extends in the direction of the core area 101 and preferably merges seamlessly with the core area 101. The first surface 103 comprises the lateral surface as well as the outer surface of the hemispherical end section of the dental implant blank 100 and is arranged entirely within the closed environment 200. The transition section 108 adjoins the implant body 105 and ends in the abutment 110, which protrudes from the closed environment. In the area of the transition section 108, the closed environment is sealed to the outer environment 300 by means of an insulation 202 (not shown), for example a silicone gasket or the like.

The outer surface 104 of the abutment 110 and the bearing surface 106 facing in the direction of the abutment of the transition section 108 are each arranged as a second surface or loading surface. For this purpose, the abutment 110 is received by a loading body 400, which is located in a loading reservoir 401. The loading body 400 is provided with a recess 402 whose shape is adapted to the dimensions of the abutment 110 in order to receive the abutment 110. The use of the loading body 400 is an optional implementation of the method. Alternatively, the loading surfaces, i.e. the outer surface 104 and/or the bearing surface 106 may also be arranged directly within the loading reservoir 401. The loading body 400 has a first loading zone 404 and a second loading zone 405, which, as described above, are suitable for receiving different solutions or identical solutions having different concentrations. According to an alternative embodiment which is not shown, the dental implant blank 100 is made in two parts. In this variant, the abutment 110 is unscrewed from the implant body 105, so that only the bearing surface 106 rests on the loading body 400. A recess 402 for receiving the abutment 110 is therefore not required. Instead of the recess 402, for example, the second loading zone 405 could be arranged to allow a parallel loading of the bearing surface 106. In this way, the core area 101 could, for example, be loaded with pure solvent 501 or with a solution 500, which in particular has cerium and/or calcium and/or zirconium, but no bioactive surface material 502, while at the same time the surface area 102 is loaded with a solution 500 comprising a bioactive surface material 502 via the same bearing surface 106. This ensures that the core area 101 remains free of bioactive surface material 502.

The loading reservoir 401 is filled with a fixed volume of a solution 500 which comprises a solvent or a dissolver 501, in particular distilled water, ethanol and/or acetic acid and a bioactive surface material or solvate 502 such as hydroxyapatite. The loading reservoir 401 is sealed against the outer environment 300 to prevent evaporation of the solvent, which would lead to a change in the concentration of the solution. Alternatively and not shown, closable inflows and outflows can be provided to allow a continuous refilling of the solution 500 or to change the concentration of the solution 500, if necessary. During the loading step, the solution 500 is supplied to the loading surfaces 104, 106 by means of the loading body 400, which has one or more loading zones 404, 405. The solution is absorbed from the loading surfaces 104, 106 due to the capillary force and/or concentration differences or environmental parameter gradients that are adjustable within the closed environment 200 relative to the loading reservoir 401. To complete the loading step, the loading reservoir 401 and the loading body 400 are removed.

During the distribution control step, which may be concurrent or subsequent to the loading step, a convection flow 503 is generated within the pores of the dental implant blank 100. For this purpose, environment parameter gradients, in particular by changing the temperature, the pressure and/or the humidity are generated within the closed environment 200. Chamber 201 has suitable means for this purpose. The solution is preferably directed to the first surface 103 or to the surface area 102 of the dental implant blank 100.

In order to start the crystallization of the bioactive material 502, drying and/or vaporization of the solvent 501 on the first surface 103 of the dental implant 100 is achieved by (hot) air nozzles 203. The temperature and the volume flow of the air supply can be controlled independently of one another. In order to discharge the supplied air and the vaporized solvent 501, chamber 201 has a ventilation flap 204. Alternatively or additionally, other venting means, such as valves, outlets or the like may be provided. By drying and/or vaporization, the concentration of the dissolved bioactive surface material 502 at the first surface 103 and within the pores of the surface area 102 is increased up to a saturation concentration. Within the pores of the surface area 102, initial crystals are formed which, starting from the first surface 103, form a crystalline layer or a crystalline surface coating 503. In order to ensure an air supply as uniformly as possible by means of the (hot) air nozzles, the loading reservoir 401 is rotatably mounted on a turntable 403, whereby the dental implant blank 100 is rotatable within the chamber 200.

In a subsequent crystal growth step, the crystalline surface coating 503 grows to the desired layer thickness. Further, during the crystal growth step, solution 500 may be loaded, the distribution of the solution 500 may be controlled by regulating environmental parameter gradients, and drying and or vaporization of the solvent 501 may be effected at the first surface 103 of the dental implant blank 100. The duration of the crystal growth step depends on the desired layer thickness as well as the amount of bioactive surface material 502 with which the dental implant blank 100 was or is loaded. A UV lamp 204 integrated in the chamber contributes to the faster curing of the crystalline surface coating 503.

In an optional coefficient of thermal expansion balancing step, the dental implant blank 100 is loaded with a balancing solution 500 containing cerium and/or zirconium and/or calcium. For this purpose, the outer surface 104 of the abutment 110 is preferably used as the loading surface, in order to introduce the balancing solution 500 in a targeted manner into the core area 101 of the dental implant blank. Alternatively, the solution can also be introduced into the core area by means of the distribution control step. The purpose of the balancing solution 500 is to remove any residues of the bioactive surface material 502 from the core area. A cleaning of the core area can also be carried out by rinsing with pure solvent 501. On the other hand, a thermal expansion coefficient balancing takes place in that the residual volume of the pores is filled with cerium and/or zirconium and/or calcium, whereby a profile of the thermal expansion coefficient starting from the first surface 103 towards the core area 101 arises.

In a final end- or densely sintering step, the dental implant blank 100 is densely sintered to the finished dental implant at temperatures around 1450° C. Here, the crystalline surface coating 503 obtains its final structure, wherein the layer thickness decreases by the sintering process.

Figure 4:
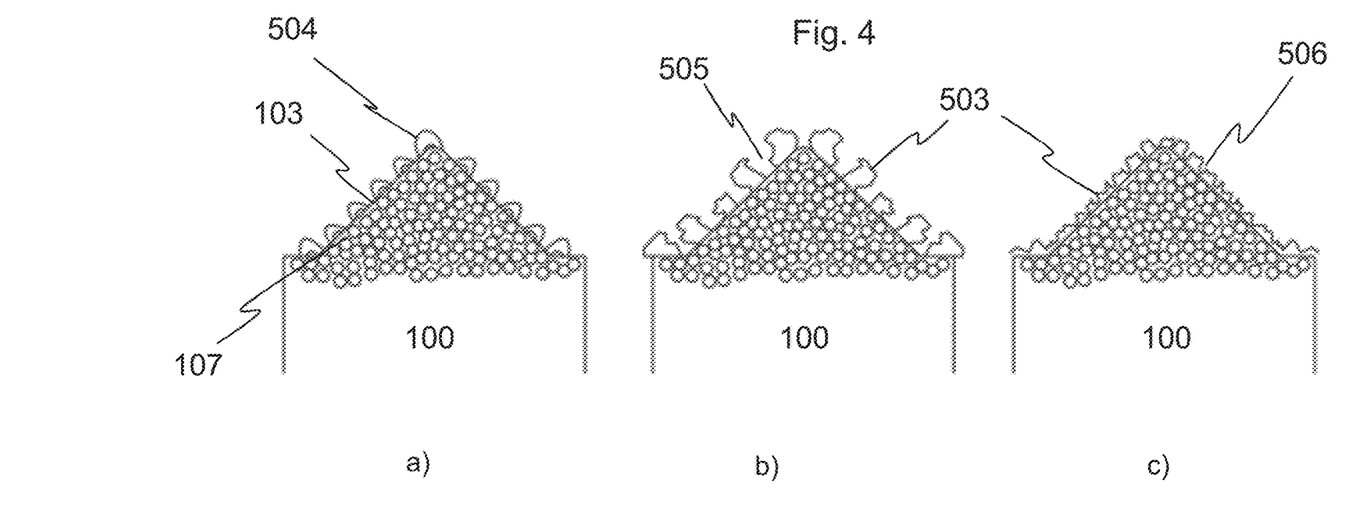
Figure 5:
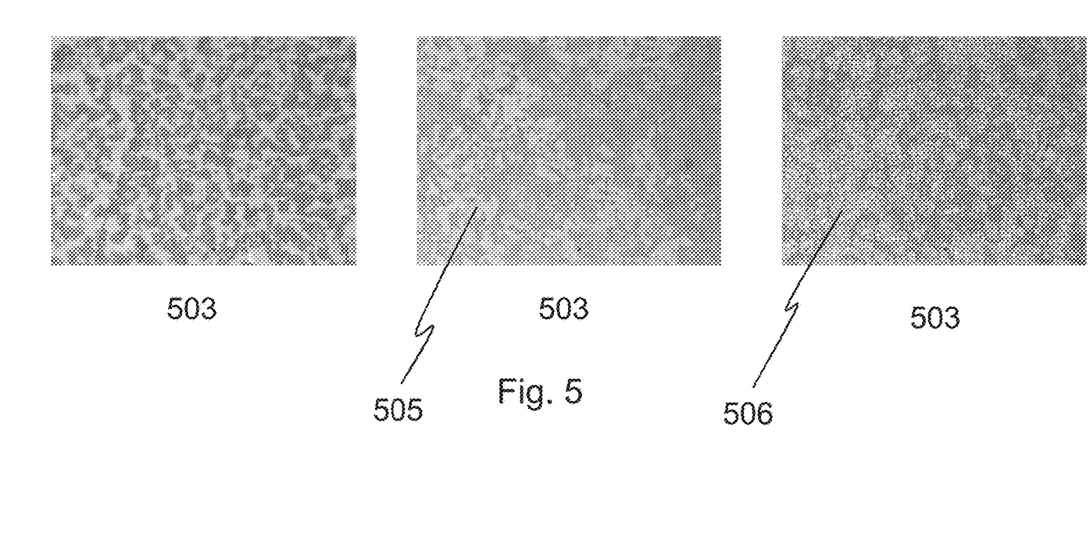
FIG. 5 shows micrographs of a crystalline, bioactive surface coating according to the growth steps from FIG. 4.

FIG. 4 schematically shows the course of the formation of a bioactive, crystalline surface coating 503 starting from a first surface 103 of a porous starting body or a dental implant blank 100. FIG. 5 in each case shows an associated microscopic image of the crystalline surface coating 503. FIGS. 4a and 5a show the formation of first crystal nuclei which form out of the pores 107 below condensed solvent droplets 504. The crystal seeds are grown after drying for 3 days on a first surface 103 of a porous zirconia ceramic. The zirconia ceramic was loaded prior with a hydroxyapatite sol (2.5 g of calcium nitrate, 1.5 g of triethyl phosphate dissolved in 40 g of ethanol). The drying was carried out in a device according to FIG. 2 at 25° C. and 30% humidity. By continuous removal of solvent, in particular by drying and/or evaporation and/or vaporization (see FIGS. 4b and 5b) for a further 48 hours, the crystal growth proceeds, whereby an increasingly dense bioactive, crystalline surface coating 503 is formed. By further increasing the duration of the growth step, a layer thickness of up to 2000 μm can be formed. Crystal interstices 505 are formed between the individual crystals, which compact by a final end-sintering at about 1450° C. to form the surface structure 506 of the bioactive, crystalline surface coating 503 (FIGS. 4c and 5c). For sintering, the implant blank 100 is placed in a sintering furnace. The temperature is increased in steps of 3° C. per minute to 1450° C. The implant blank 100 remains for about 2.5 hours at this temperature in the sintering furnace. Subsequently, the temperature in the oven is lowered in steps of 3° C. per minute to 200° C.

Figure 6:
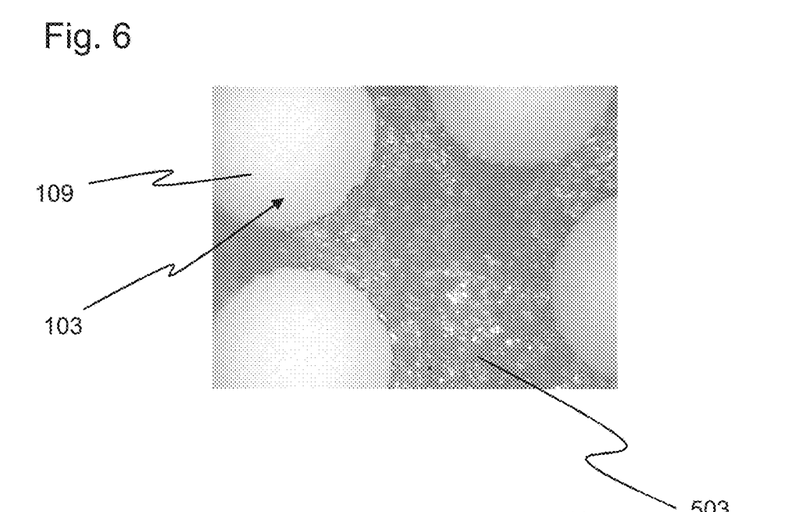
FIG. 6 shows a micrograph of a crystalline surface coating with isolated areas.

FIG. 6 shows a micrograph of a crystalline surface coating 503, wherein individual areas 109 of the first surface 103 of the starting body 100 have been isolated from crystal growth or the formation of the crystalline surface coating 503. The diameter of an isolated area 109 is about 0.30 mm. The starting body used was a porous zirconia ceramic which was infiltrated or loaded with a hydroxyapatite sol. The hydroxyapatite sol used was prepared from 20 g of calcium nitrate, 20 g of distilled water and 12.8 g of triethyl phosphate. At the time of the absorption, the starting body had been subjected to crystal growth at 25° C. and 30% humidity already for 3 days in a device according to FIG. 2. Prior to loading, the areas 109 were isolated by paint application by means of a printer to prevent crystal growth. However, the isolation of the areas 109 can also be effected in other ways, for example by coating or by applying a film.

Figure 7:
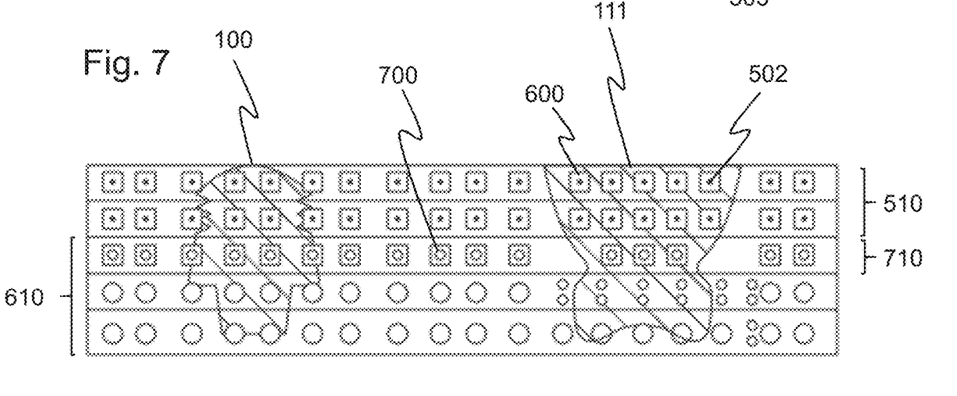
FIG. 7 is a schematic representation of an alternative embodiment of the method according to the invention.

In FIG. 7, an alternative variant of the method is shown schematically. As a starting body, for example, a cylindrical, plate-shaped, porous blank made of metal or ceramic is used. The blank is loaded simultaneously or sequentially with different solutions. Preferably, at least one first solution contains a bioactive, crystallizable surface material 502, at least one second solution of a chemical substance for affecting physical properties 600, for example for affecting the hardness, and at least one third solution of coloring components 700. The distribution of the respective solutions can be controlled in such a way that areas with an increased concentration of bioactive material, areas with increased concentration of hardness-reducing stabilizers 610 and areas with increased concentration of coloring components 710, for example for coloring with the gingival color pink, form. From the plate-shaped blank then a dental implant blank 100 and/or a dental prosthesis blank or also a jaw bone replacement blank 111 may be milled by CAD/CAM and subjected to the remaining process steps.

1 dental prosthesis
2 dental implant
3 tooth
4 tooth root
5 implant body
6 external thread
7 jaw bone
8 transition section
9 gums
10 abutment
100 porous starting body/dental implant blank
101 core area
102 surface area
103 first surface
104 outer surface, loading surface
105 implant body
106 bearing surface, loading surface
107 pores
108 transition section
109 area of the first surface
110 abutment
111 dental prosthesis blank/jaw bone replacement blank
200 closed environment
201 chamber
202 insulation
203 (hot) air nozzle
204 UV lamp
300 outer environment
400 loading body
401 loading reservoir
402 recess
403 turntable
404 first loading zone
405 second loading zone
500 solution
501 solvent/dissolver
502 bioactive surface material/solvate
503 crystalline layer/crystalline surface coating
504 solvent drop
505 crystal interstices
506 surface structure
510 area with increased concentration of bioactive material
600 chemical substance for affecting physical properties
610 area with increased concentration of hardness-lowering stabilizers
700 coloring components
710 area with increased concentration of coloring components

The invention claimed is:

1. A method for producing an implant blank (100) from a starting body, said implant blank (100) comprising at least one first area, which is a surface area (102), and a second area, which is a core area (101), wherein the surface area (102) has at least one bioactive surface material (502) and extends from at least one first surface (103) in the direction of the core area (101), and the core area (101) has at least one carrier material that can be subjected to mechanical load, characterized in that the starting body has a porosity for controlling a targeted distribution of the bioactive surface material (502) within the starting body and is loaded with a solution (500) of the bioactive surface material (502) in a first step, which is a loading step, and in a second step, which is a distribution control step, the distribution of the bioactive surface material (502) within the starting body is controlled such that the solution (500) has a higher concentration within the surface area (102) than within the core area (101), the control being effected by regulating one or more environmental parameters in a sealed closed environment (200), wherein the distribution of the bioactive surface material (502) is effected within the starting body by a convection current, and wherein a direction of flow and velocity are controlled by targeted generation of environmental parameter gradients by adjusting humidity differences or pressure differences or temperature differences with respect to different surfaces of the starting body.

2. The method according to claim 1, characterized in that the loading of the starting body with the solution (500) of the at least one bioactive surface material (502) is effected via at least one second surface of the starting body, which is a loading surface (104, 106), wherein the loading surface (104, 106) is a surface other than the first surface (103).

3. The method according to claim 2, characterized in that the loading surface (104, 106) for loading the starting body with the bioactive surface material (502) is arranged outside the closed environment (200).

4. The method according to claim 2, characterized in that the concentration of the solution (500) is constant during the loading step or during the loading of the starting body.

5. The method according to claim 2, characterized in that the bioactive surface material (502) is crystallizable, and is crystallized in a third step, which is a crystallization step within the surface area (102) or in the area of the first surface (103).

6. The method according to claim 5, characterized in that the bioactive surface material (502) is form-fittingly or force-fittingly arranged within pores (107) of the surface area (102) of the starting body.

7. The method according to claim 6, characterized by a crystal-growing step, wherein crystals of the bioactive surface material (502) grow from the porosity of the surface area (102) to a crystalline layer (503), said crystalline layer (503) covering at least a portion of the first surface (103) of the starting body.

8. The method according to claim 7, characterized by a pore-forming step, wherein the crystals or the crystalline layer (503) of the bioactive material (502) are subjected to a heat treatment forming pores or increasing the surface roughness (506).

9. The method according to claim 7, characterized in that a morphology or structure (506) or surface (506) or porosity of the crystalline layer (503) or of the crystals of the bioactive surface material (502) are affected by the solvent (500).

10. The method according to claim 2, characterized by a coefficient of thermal expansion balancing step, wherein the starting body is rinsed with a balancing solution having zirconium or calcium or cerium.

11. The method according to claim 2, characterized by a sintering step, wherein by the sintering step, a material bond or a chemical bond between the bioactive surface material (502) and the carrier material is generated.

12. The method according to claim 1, characterized in that the concentration or a concentration profile of the solution (500) is controlled within the starting body by drying or vaporization.

13. The method according to claim 1, characterized by the following steps, (A) providing the porous starting body (B) placing the first surface (103) of a starting body within a closed environment (200), wherein at least a portion of a second surface (104, 106) of the starting body, which is a loading surface (104, 106), is located outside the closed environment (200), (C) loading the loading surface (104, 106) of the starting body with the bioactive surface material (502), wherein the bioactive surface material (502) is dissolved in a solvent (500), (D) controlling the distribution of the bioactive surface material (502), wherein the solution (500) has a higher concentration within the surface area (102) than within the core area (101) and the humidity or the pressure or the temperature is regulated to generate an environmental parameter gradient, (E) crystallizing the bioactive surface material (502), wherein the concentration of the solution (500) within the surface area (102) is increased by vaporization or evaporation or drying, and (F) forming a crystalline layer (503) of the bioactive surface material (502) by crystal growth.

14. The method according to claim 1, characterized in that the implant blank (100) is a dental implant blank.

15. The method according to claim 1, characterized in that the control of the targeted distribution being effected by regulating the humidity or the pressure or the temperature.

* * * * *